United States Patent
Gündel

(10) Patent No.: US 7,809,176 B2
(45) Date of Patent: Oct. 5, 2010

(54) DEVICE AND METHOD FOR AUTOMATED PLANNING OF AN ACCESS PATH FOR A PERCUTANEOUS, MINIMALLY INVASIVE INTERVENTION

(75) Inventor: Lutz Gündel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1097 days.

(21) Appl. No.: 11/498,763

(22) Filed: Aug. 4, 2006

(65) Prior Publication Data

US 2007/0049861 A1    Mar. 1, 2007

(30) Foreign Application Priority Data

Aug. 5, 2005    (DE)    ................... 10 2005 037 000

(51) Int. Cl.
*G06K 9/00* (2006.01)
*G06K 9/34* (2006.01)
(52) U.S. Cl. .................................. 382/128; 382/173
(58) Field of Classification Search .............. 604/27; 600/416, 423–427; 345/418–419, 474; 382/128, 382/131–132, 153, 173; 128/897–899; 700/56–61
See application file for complete search history.

(56) References Cited

U.S. PATENT DOCUMENTS

| | | | | |
|---|---|---|---|---|
| 6,671,538 B1 * | 12/2003 | Ehnholm et al. | ............ | 600/425 |
| 7,167,180 B1 * | 1/2007 | Shibolet | ..................... | 345/474 |
| 2003/0109780 A1 | 6/2003 | Coste-Maniere et al. | | |
| 2004/0234933 A1 | 11/2004 | Dawson et al. | | |

FOREIGN PATENT DOCUMENTS

| | | |
|---|---|---|
| DE | 698 05 209 T2 | 11/2002 |
| WO | WO 2005/009215 A2 | 2/2005 |
| WO | WO 2005/055008 A2 | 6/2005 |

OTHER PUBLICATIONS

Adhami et al. "Optimal planning for minimally invasive surgical robots", IEEE Trans on Robotics and Automation, vol. 19, No. 5, 2003.*
Lombardo et al. "Real-time collision detection for virtual surgery", Proceedings of the Computer Animation, p. 82, 1999.*

* cited by examiner

*Primary Examiner*—Tom Y Lu
*Assistant Examiner*—Thomas A Conway
(74) *Attorney, Agent, or Firm*—Harness, Dickey & Pierce, P.L.C.

(57) ABSTRACT

A device and a method are disclosed for automated planning of an access path for a percutaneous, minimally invasive intervention on an area of the body, in particular on the lungs. In the method, 3D image data of the body area are prepared, from which bones and elements endangered by the intervention are automatically segmented. In a display of the 3D image data and/or of image data derived therefrom, a target position is marked in the 3D image data by a user. On the basis of one or more predefined path geometries, the target position and the segmented data, a planning module automatically determines one or more access paths to the target position which do not run through bones and which do not intersect any elements endangered by the intervention, or intersect only a minimal number of elements endangered by the intervention. The one or more access paths are presented to the user on a monitor for information and/or interactive selection and/or correction in a display of the 3D image data or of image data derived therefrom.

25 Claims, 1 Drawing Sheet

DEVICE AND METHOD FOR AUTOMATED PLANNING OF AN ACCESS PATH FOR A PERCUTANEOUS, MINIMALLY INVASIVE INTERVENTION

PRIORITY STATEMENT

The present application hereby claims priority under 35 U.S.C. §119 on German patent application number DE 10 2005 037 000.4 filed Aug. 5, 2005, the entire contents of which is hereby incorporated herein by reference.

FIELD

The present invention generally relates to a device and/or a method for automated planning of an access path for a percutaneous, minimally invasive intervention on a body area, in particular the lungs.

BACKGROUND

Percutaneous, minimally invasive interventions represent an operating technique that is particularly gentle on the patient. In a biopsy or in another minimally invasive intervention on the lungs, for example, a needle is pushed into the thoracic cage and guided to the target position. There, the tissue is removed or the intended operation performed. The needle is then withdrawn again, so that only the small puncture site remains. In interventions of this kind on the lungs, however, vessels are often damaged, as a result of which internal bleeding can occur, which subsequently has to be stopped. If fairly large bronchi are encountered on the access path to the target position, air can get into the lung tissue and cause what is known as a pneumothorax, which requires subsequent treatment.

At present, the planning of the puncture site is carried out by way of imaging techniques, generally by way of computed tomography. Starting from the target position and extending past the ribs, a suitable puncture site on the skin is sought in the 3D image data of the computed tomography apparatus. Vessels and bronchi on the access path between the puncture site and the target position are in most cases not taken into account in the planning. Particularly in the case of lesions lying directly behind the ribs or of deeper-lying target positions, this method proves to be susceptible to errors and, in the event of an error occurring, leads to the procedure having to be repeated, which is time-consuming and places a burden on the patient.

SUMMARY

A device and a method are made available that permit automated planning of an access path for a percutaneous, minimally invasive intervention on an area of the body, particularly the lungs.

In at least one embodiment, the present device is for automated planning of an access path for a percutaneous, minimally invasive intervention on an area of the body, particularly the lungs. The device comprises, in addition to a storage unit for storing 3D image data of the body area, at least one segmentation module, a planning module, a display module and an interaction module.

The segmentation module automatically segments bones and skeletal parts, for example the ribs, shoulder or vertebral column, vessels and, if appropriate, other elements endangered by the intervention, for example bronchi, in the stored 3D image data. The 3D image data can in this case originate from a suitable 3D-imaging system, in particular a computed tomography apparatus or a magnetic resonance tomography apparatus. Of course, image data from other imaging systems are also possible, as long as these permit segmentation of the bones, vessels and other elements endangered by the intervention in the image data. The segmentation itself takes place in a known manner using suitable segmentation techniques which, in the simplest case, are based on threshold values. From the processing of medical images, numerous segmentation techniques for this purpose are known to a person skilled in the art.

On the basis of one or more predefined path geometries, the target position and the segmented bones and elements, the planning module automatically determines one or more access paths to the target position which do not run through bones and which do not intersect any vessels and other endangered elements, or intersect only a minimal number of such vessels and other elements. The path geometries, for example a rectilinear path or a curved path with a specific radius, can either be predefined by the user or can be offered to the user of the device for selection. A rectilinear path is generally chosen in an intervention using a rectilinear and rigid instrument, for example a rigid needle or a rigid trocar.

In the case of curved instruments, for example a curved needle, a suitably curved path geometry can accordingly be predefined. The same applies to the use of thin needles which, because of their lack of strength, bend during the intervention.

On the basis of these predefined path geometries, the planning module calculates one or more suitable access paths to the target position. This calculation is made possible by knowing the position of the bones, vessels and other elements from the segmentation step, for example of the ribs (possibly also of the vertebral column and shoulder), vessels and bronchi in the case of the lungs, the position of the skin surface from the 3D image data and the three-dimensional position of the puncture site, which can be marked in advance by the user in a display of the three-dimensional image data set.

Determining the suitable three-dimensional access paths in this case simply represents a geometric problem that can be solved by suitable algorithms. In one example, a large number of uniformly distributed start positions on the skin surface can be predefined which are each connected to the target position in the predefined path geometry. In a further example, the reverse course is followed. Starting from the position of the lesion, a family of different paths is arranged in the defined path geometry in the direction of the skin surface.

From the number of available access paths in both examples, the path or paths that do not run through bones or skeletal parts and do not intersect any of the segmented elements, in particular vessels or bronchi, are then chosen. The one or more access paths are determined such that, as far as possible, i.e. for the greatest possible number of vessels, a predefined clearance distance from the vessels is maintained which is dependent on a diameter of the vessels. In addition, it is possible, in both examples, when there are several suitable access paths, to choose only the path or paths offering the shortest access route and/or the smallest risk of injury.

The display module is used for displaying the 3D image data and/or image data derived therefrom and for displaying the access paths determined by the planning module in the 3D image data and/or image data derived therefrom. The derived image data can, for example, involve an MPR display (MPR: multiplanar reformatting). Closely associated with the display module, there is an interaction module which has a user interface and which is configured for interactive selection and/or for correction of the access paths determined by the planning module, and for marking of a target position in a display of the 3D image data or the image data derived therefrom.

The user can therefore use the interaction module to mark the desired target position of the minimally invasive intervention in the displayed 3D image data set. This target position is then taken over into the planning module in order to determine suitable access paths. Moreover, in cases where there are several suitable access paths, the interaction module can be used to select one of these access paths in the display or also to subsequently correct it. Of course, the display of the 3D image data can be suitably adapted by the user, in particular enlarged, reduced in size, shifted or turned. All techniques for displaying three-dimensional image data can be implemented for this purpose. The planning module preferably also comprises an interface via which it is possible to transfer lesion coordinates from other applications, for example computer-aided detection tools.

The method and the device are described below mainly on the basis of the preferred use in an intervention on the lungs where, for example, the ribs, as representative of bones, and vessels and bronchi, as representative or elements endangered by the intervention, are segmented and taken into account in the planning. However, the description below can also readily be applied to other body areas, for example to interventions in the neck area.

In example embodiments of the device, the planning module is configured such that, when determining or calculating the access paths, it takes account of a predefined clearance distance between the paths and the ribs. This clearance distance can be predefined in the device or can also be input in advance by the user via the interaction module. The same applies to clearance distances from the vessels and/or bronchi. These clearance distances must be greater, the larger the diameter of the corresponding vessels and/or bronchi. The clearance distance stored in the device, or input by the user, is thus fixed or chosen as a function of the diameter of the affected bronchi and/or vessels. The diameter of the bronchi and/or vessels which the access path runs past can in turn be automatically determined from the segmented data.

When planning the access path, it can happen that the planning module does not find any suitable access path that does not intersect any vessels and/or bronchi and that offers sufficient clearance distance from vessels and/or bronchi. In this case, the user is shown the access path or access paths that intersect the smallest number of vessels and/or bronchi. A multiplanar reconstruction perpendicular to the planned access path visualizes the potential risk of injury. The access paths are in this case preferably displayed with visual highlighting so that the user can discern, within the display, the position and or size and diameter of the affected bronchi and/or vessels that are intersected by the access path. The visual highlighting can be done by colored marking, for example. This provides the user with a rapid overview and risk assessment in the choice of this access path.

From the display of the one or more suitable access paths, the user is in each case able to discern at what puncture site he must begin the intervention and in which direction the puncture must be made. When using an instrument, for example a biopsy needle, with a position sensor attached to it in which the position of the tip of the instrument can be recorded and displayed via a navigation system during the intervention, the intervention can also be additionally monitored. For this purpose, the three-dimensional position of the tip of the instrument, as recorded by the navigation system, is inserted into the display of the three-dimensional image data set or the image data derived therefrom, preferably in each case with the selected access path. This allows the user to exactly position and guide the instrument in accordance with the selected access path. Of course, the navigation system must in this case be accordingly registered with the 3D image data in the device. Such registration, i.e. assignment of the three-dimensional coordinate systems of the navigation system and of the 3D image data, is adequately known to a person skilled in the art from imaging techniques in medicine.

The device in at least one embodiment, and the associated method according to which the device operates in at least one embodiment, therefore allow automated access planning for a percutaneous, minimally invasive intervention on the lungs. For this purpose, only a three-dimensional image data set of the lungs is needed, as can be recorded, for example, with a computed tomography apparatus. Moreover, in the simplest configuration, the user simply has to mark the target position in a display of the three-dimensional image data, and this target position is then taken over by the planning module. One or more suitable access routes are then displayed to the user by the display module, generally on a monitor. By means of this automated planning, it is possible to largely avoid damage to vessels or bronchi caused by inaccurate planning, thereby removing the need for costly follow-up treatment.

BRIEF DESCRIPTION OF THE DRAWINGS

The device and the associated method are briefly explained below on the basis of an illustrative embodiment that does not limit the scope of protection of the patent claims, with reference being made to the drawings, in which:

DETAILED DESCRIPTION OF THE EXAMPLE EMBODIMENTS

Figure 1:
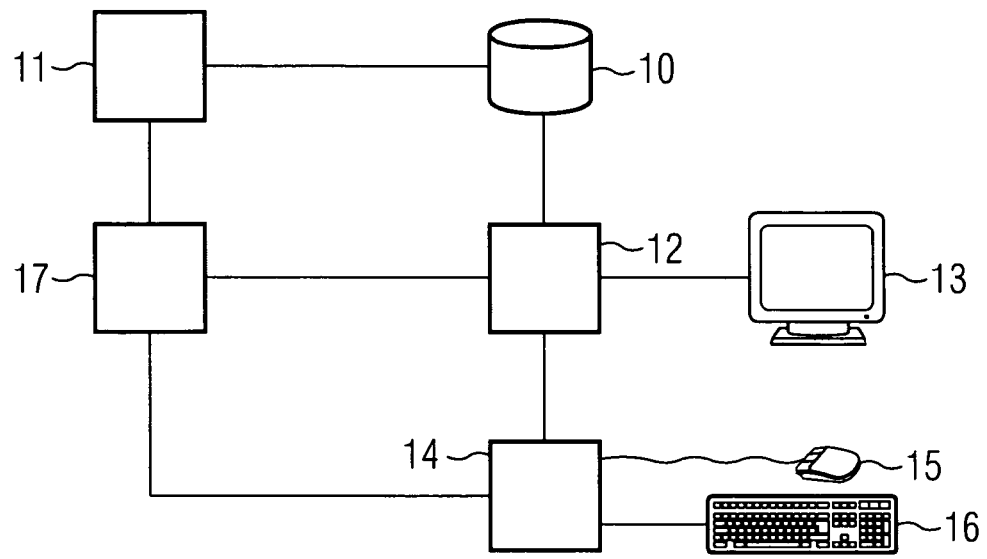
FIG. 1 shows a schematic view of the individual modules of an example embodiment of the device.

An aim of at least one embodiment of the method described by way of example below is to make it possible, in a manner that does not place a burden on the patient, to implement an automated access plan for a percutaneous lung biopsy. This makes use of a three-dimensional data set 1 of the lungs which has been recorded in a defined respiratory phase by way of a computed tomography apparatus. This three-dimensional data set 1 (cf. FIG. 2) is stored in the storage unit 10 of the device, as is shown in FIG. 1. The device in this case also includes a display module 12 with a display screen 13, an interaction module 14, in the present example with a mouse 15 and a keyboard 16, a segmentation module 11 and a planning module 17.

Figure 2:
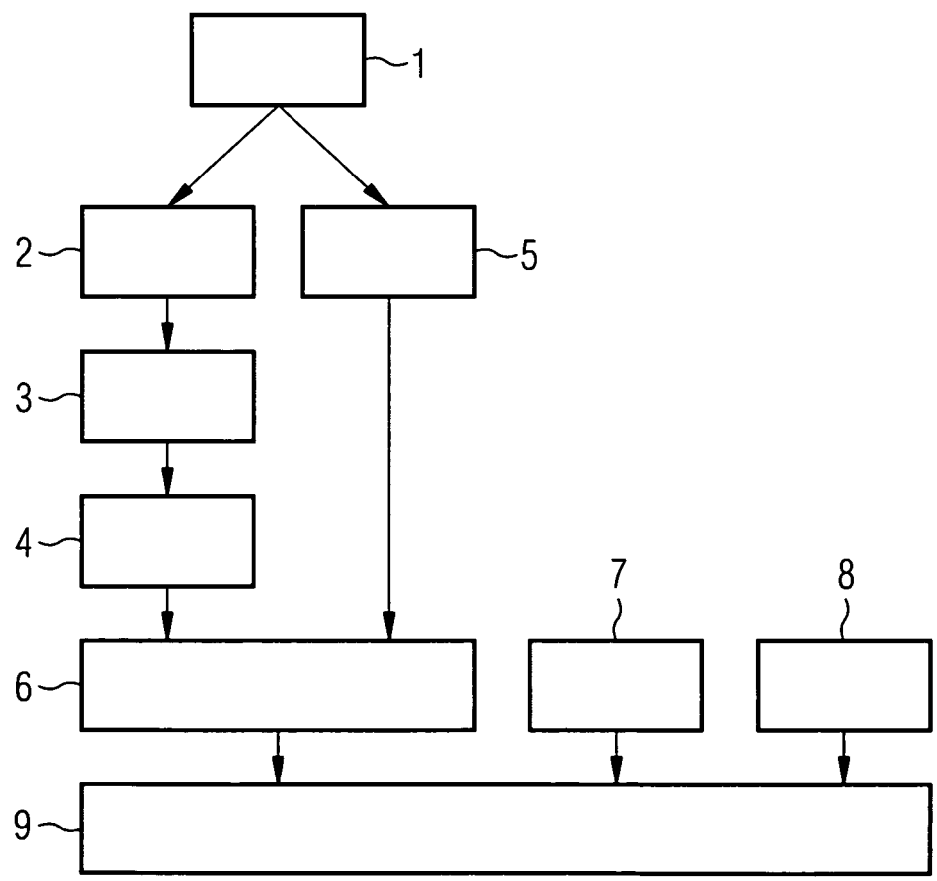
FIG. 2 shows an example of the method sequence involved in an example embodiment of the method.

As is shown in FIG. 2, the segmentation module 11 performs an automatic segmentation of the ribs 2, an automatic segmentation of the bronchi 3, and an automatic segmentation of the vessels 4 in the stored three-dimensional data set 1. In addition, the segmentation module 11 can also determine the lobes of the lung and the bronchopulmonary segments, if this is necessary for the intervention. At the same time as the segmentation, before the start of the segmentation or after the segmentation, the user employs the interaction module 14 to mark the target of the intervention in the three-dimensional image set 1 displayed on the monitor 13.

After the segmentation steps and the target marking 5, the automatic planning of the access path takes place in the planning module 17 in such a way that the fewest possible bronchi and vessels lie on the access path and there is as short as possible and as straight as possible a connection between the required puncture site and the target position, said connection running past the ribs with a clearance distance. A suitable clearance distance can be predefined according to the size of the vessels and bronchi. If so desired, a curved path can also be planned instead of the rectilinear access path. In doing so, account is taken of the possible bending radius of thin needles which, because of their lack of strength, can bend during the intervention. Of course, needles can also be taken into account in which the bending radius is predefined, that is to say desired. The access path or paths found are presented to the user on the monitor 13 and can be selected by him and, if appropriate, modified in a suitable way. The path planning and display and the interactive modification are combined in step 6 in FIG. 2.

If no suitable path is found, the user is presented with alternatives in which injuries to the vessels and/or bronchi cannot be excluded. At the same time, in order to permit a risk assessment, the vessels and bronchi lying on the corresponding access path, their diameter and their position, are displayed on the monitor 13 with colored highlighting. The user can then decide which of the proposed access paths, if any, to choose.

During the intervention, the respiratory phase of the patient is determined by means of suitable procedures in step 7 and presented to the user. In this way, he can carry out the intervention in the same phase in which the measurement of the three-dimensional data set 1 also took place. In this way, it is possible to ensure a minimal error between the anatomical conditions during imaging and during the intervention. If, in parallel with the intervention, the position of the needle tip is determined by means of a navigation tool, as is represented by step 8, this can be integrated into the 3D data set presented on the monitor 13 during the intervention, thus making the intervention easier. This joint display of planning and intervention corresponds to step 9 in FIG. 2.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for automated planning of an access path for a percutaneous, minimally invasive intervention on an area of the body, comprising:

a storage unit to store 3D image data of the body area;

a segmentation module to automatically segment bones, vessels, and, if appropriate, other elements endangered by the intervention in the 3D image data;

a planning module to, on the basis of at least one predefined path geometry, a target position and the segmented bones, vessels and other elements endangered by the intervention, automatically determine at least one access path to the target position, the planning module being configured such that the at least one access path maintains a clearance distance from the vessels which is dependent on a diameter of the vessels;

a display module to display at least one of the 3D image data and image data derived from the 3D image data and to display the at least one access path determined by the planning module in at least one of the 3D image data and image data derived from the 3D image data; and an interaction module, including a user interface, usable for at least one of interactive selection and correction of the at least one access path determined by the planning module, and to mark a target position in a display of at least one of the 3D image data and the image data derived from the 3D image data; wherein the at least one access path to the target position does not run through bones and does not intersect any vessels and other elements endangered by the intervention, and if at least one access path to the target position that does not run through bones and does not intersect any vessels and other elements endangered by the intervention is not found, the at least one access path to the target position intersects only a set number of vessels and other elements endangered by the intervention.

2. The device as claimed in claim 1 for automated planning of an access path for a percutaneous, minimally invasive intervention on the lungs, wherein the segmentation module automatically segments skeletal parts, vessels and bronchi in the 3D image data, and the planning module automatically determines at least one access path to the target position which does not run through skeletal parts and which does not intersect any vessels and bronchi, or intersects only a small number of vessels and bronchi.

3. The device as claimed in claim 1, wherein the planning module is configured such that the at least one access path determined by the planning module maintains a clearance distance from the bones or skeletal parts.

4. The device as claimed in claim 1, wherein the planning module is configured such that the at least one access path determined by the planning module maintains a clearance distance from bronchi, which clearance distance is dependent on a diameter of the bronchi.

5. The device as claimed in claim 1, wherein the interaction module is configured to input the clearance distance from at least one of the vessels, the bones and the skeletal parts, on the basis of which the planning module determines the at least one access path.

6. The device as claimed in claim 1, wherein the display module is configured such that, when the at least one access path determined by the planning module intersects vessels or at least does not maintain a clearance distance from them, the display module displays at least one of the affected vessels and their position and diameter with visual highlighting.

7. The device as claimed in claim 1, wherein, when the percutaneous, minimally invasive intervention involves using a navigation system that delivers to the device an instantaneous position of a tip of the instrument used for the intervention, the display module is configured such that it presents the instantaneous position in a display of the 3D image data or of image data derived from the 3D image data.

8. The device as claimed in claim 1, wherein the interaction module is configured for inputting the path geometries, on the basis of which the planning module determines the at least one access path.

9. The device as claimed in claim 1, wherein the planning module is configured such that it determines the at least one access path on the premise of at least one of the shortest route and a single-curve route to the target position.

10. The device as claimed in claim 2, wherein the planning module is configured such that the at least one access path determined by the planning module maintains a clearance distance from the bones or skeletal parts.

11. The device as claimed in claim 2, wherein the planning module is configured such that the at least one access path determined by the planning module maintains a clearance distance from bronchi, which clearance distance is dependent on a diameter of the bronchi.

12. A tangible computer readable medium including program segments for, when executed on a computer, causing the computer to implement the method of claim 1.

13. A method for automated planning of an access path for a percutaneous, minimally invasive intervention on an area of the body, comprising:
preparing 3D image data of the body area;
automatically segmenting bones, vessels, and, if appropriate, other elements endangered by the intervention from the 3D image data;
marking a target position in at least one of a display of the 3D image data and image data derived from the 3D image data;
automatically determining, on the basis of path geometries, the target position and the segmented bones, vessels and other elements endangered by the intervention, at least one access path such that a clearance distance from the vessels is maintained which is dependent on a diameter of the vessels; and
displaying the at least one access path for at least one of information, interactive selection and correction in a display of the 3D image data or of image data derived from the 3D image data; wherein
the at least one access path does not run through bones and does not intersect any vessels and other elements endangered by the intervention, and
if at least one access path that does not run through bones and does not intersect any vessels and other elements endangered by the intervention is not found, the at least one access path intersects only a set number of vessels and other elements endangered by the intervention.

14. The method as claimed in claim 13 for automated planning of an access path for a percutaneous, minimally invasive intervention on the lungs, in which skeletal parts, vessels and bronchi are automatically segmented from the 3D image data, and at least one access path to the target position is determined which does not run through skeletal parts and which does not intersect any vessels or bronchi, or intersects only a minimal number of vessels and bronchi.

15. The method as claimed in claim 13, wherein the at least one access path is determined such that a clearance distance from the bones or skeletal parts is maintained.

16. The method as claimed in claim 13, wherein the at least one access path is determined such that a clearance distance from bronchi is maintained which is dependent on a diameter of the bronchi.

17. The method as claimed in claim 13, wherein at least one of the clearance distance from at least one of the vessels, bones, skeletal parts and bronchi is defined by a user.

18. The method as claimed in claim 13, wherein, when access paths are determined which intersect at least one of vessels and bronchi or which at least do not maintain a clearance distance, the user is provided with a display in which the at least one of the affected vessels, bronchi and their position and diameter are shown with visual highlighting.

19. The method as claimed in claim 13, wherein, when the percutaneous, minimally invasive intervention involves using a navigation system that delivers an instantaneous position of a tip of the instrument used for the intervention, the instantaneous position is presented to the user in a display of at least one of the 3D image data and image data derived from the 3D image data.

20. The method as claimed in claim 13, wherein the user defines or selects the at least one path geometry.

21. The method as claimed in claim 13, wherein the at least one access path is determined under the premise of at least one of the shortest route and a single-curve route to the target position.

22. The method as claimed in claim 14, wherein the at least one access path is determined such that a clearance distance from the bones or skeletal parts is maintained.

23. The method as claimed in claim 14, wherein the at least one access path is determined such that a clearance distance from bronchi is maintained which is dependent on a diameter of the bronchi.

24. The method as claimed in claim 14, wherein at least one of the clearance distance from at least one of the vessels, bones, skeletal parts and bronchi is defined by a user.

25. A device for automated planning of an access path for a percutaneous, minimally invasive intervention on an area of the body, comprising:
means for storing 3D image data of the body area;
means for automatically segment bones, vessels, and, if appropriate, other elements endangered by the intervention in the 3D image data;
planning means for, on the basis of at least one predefined path geometry, a target position and the segmented bones, vessels and other elements endangered by the intervention, automatically determining at least one access path to the target position, the planning means being configured such that the at least one access path determined by the planning means maintains a clearance distance from the vessels which is dependent on a diameter of the vessels;
means for displaying at least one of the 3D image data and image data derived from the 3D image data and for displaying the at least one access path determined by the planning means in at least one of the 3D image data and image data derived from the 3D image data; and means, including a user interface, for at least one of interactive selection and correction of the at least one access path determined by the planning means, and for marking a target position in a display of at least one of the 3D image data and the image data derived from the 3D image data; wherein the at least one access path to the target position does not run through bones and does not intersect any vessels and other elements endangered by the intervention, and if at least one access path to the target position that does not run through bones and does not intersect any vessels and other elements endangered by the intervention is not found, the at least one access path to the target position intersects only a set number of vessels and other elements endangered by the intervention.

* * * * *